US012616661B2

(12) United States Patent
Bleiel et al.

(10) Patent No.: US 12,616,661 B2
(45) Date of Patent: May 5, 2026

(54) COMPOSITION FOR TYPE II DIABETICS AND FOR USE IN PROVIDING SUSTAINED ENERGY RELEASE OVER TIME

(71) Applicant: AnaBio Technologies Ltd., County Cork (IE)

(72) Inventors: Sinead Bleiel, Dublin (IE); Robert Kent, Cork (IE); Neil Gerard Docherty, Dublin (IE); Carel Wynand Le Roux, Dublin (JE)

(73) Assignee: TEAGASC—The Agriculture and Food Development Authority, Carlow (IE)

( * ) Notice: Subject to any disclaimer, the term of this patent is extended or adjusted under 35 U.S.C. 154(b) by 1097 days.

(21) Appl. No.: 16/978,587

(22) PCT Filed: Mar. 7, 2019

(86) PCT No.: PCT/EP2019/055792
§ 371 (c)(1),
(2) Date: Sep. 4, 2020

(87) PCT Pub. No.: WO2019/170840
PCT Pub. Date: Sep. 12, 2019

(65) Prior Publication Data
US 2021/0100749 A1 Apr. 8, 2021

(30) Foreign Application Priority Data
Mar. 7, 2018 (EP) ..................................... 18160601

(51) Int. Cl.
*A61K 9/50* (2006.01)
*A23L 33/00* (2016.01)
(Continued)

(52) U.S. Cl.
CPC .......... *A61K 9/5052* (2013.01); *A23L 33/125* (2016.08); *A23L 33/18* (2016.08);
(Continued)

(58) Field of Classification Search
CPC ................ A61K 9/5052; A61K 9/0053; A61K 31/7016; A23L 33/125; A23L 33/18;
(Continued)

(56) References Cited

U.S. PATENT DOCUMENTS

| | | | |
|---|---|---|---|
| 2010/0173002 A1 | 7/2010 | Yulai et al. | |
| 2021/0077386 A1 | 3/2021 | Bleiel et al. | |
| 2022/0040258 A1 | 2/2022 | Bleiel | |

FOREIGN PATENT DOCUMENTS

| | | |
|---|---|---|
| CA | 2654031 A1 | 2/2008 |
| CN | 107405310 A | 11/2017 |

(Continued)

OTHER PUBLICATIONS

Kuhre et al., Fructose stimulates GLP-1 but not GIP secretion in mice, rats, and humans, 2014, Am J Physiol Gastroinest Liver Physiol., 306(7): G622-G630, 16 pages. (Year: 2014).*

(Continued)

*Primary Examiner* — Trevor Love
(74) *Attorney, Agent, or Firm* — HAMILTON, BROOK, SMITH & REYNOLDS, P.C.

(57) ABSTRACT
A composition for use in a method of providing sustained energy release over time in a subject is described. The composition comprises or consists of microparticles comprising high glycaemic index (GI) carbohydrate contained within a gastric-resistant, ileal-sensitive, GLP-1 stimulative, non-porous carrier configured for release of the high GI carbohydrate in the ileum, wherein the composition is administered orally to the subject.

20 Claims, 12 Drawing Sheets

(51) Int. Cl.

| | |
|---|---|
| *A23L 33/125* | (2016.01) |
| *A23L 33/18* | (2016.01) |
| *A23L 33/185* | (2016.01) |
| *A23L 33/19* | (2016.01) |
| *A23P 10/30* | (2016.01) |
| *A61K 9/00* | (2006.01) |
| *A61K 31/7016* | (2006.01) |
| *A61P 3/10* | (2006.01) |

(52) U.S. Cl.
CPC ............. *A23L 33/185* (2016.08); *A23L 33/19* (2016.08); *A23L 33/40* (2016.08); *A23P 10/30* (2016.08); *A61K 9/0053* (2013.01); *A61K 31/7016* (2013.01); *A61P 3/10* (2018.01); *A23V 2002/00* (2013.01)

(58) Field of Classification Search
CPC ........ A23L 33/185; A23L 33/19; A23L 23/40; A23P 10/30; A23P 3/10; A23V 2002/00
See application file for complete search history.

(56) References Cited

FOREIGN PATENT DOCUMENTS

| | | | |
|---|---|---|---|
| WO | 2004105520 A1 | 12/2004 |
| WO | 2009053487 A2 | 4/2009 |
| WO | 2010/027498 A2 | 3/2010 |
| WO | 2010/119041 A2 | 10/2010 |
| WO | 2013/063527 A1 | 5/2013 |
| WO | 2014198787 A1 | 12/2014 |
| WO | 2016020217 A1 | 2/2016 |
| WO | 2016/096929 A1 | 6/2016 |
| WO | 2016096931 A1 | 6/2016 |
| WO | 2016/178202 A1 | 11/2016 |
| WO | 2016/185053 A1 | 11/2016 |
| WO | 2016/205754 A1 | 12/2016 |
| WO | 2016193373 A1 | 12/2016 |
| WO | 2019/170839 A2 | 9/2019 |

OTHER PUBLICATIONS

FAO, Chapter 3, FAO Food and Nutrition Paper 77, Food Energy—methods of analysis and conversion factors, Food and Agriculture Organization of the United Nations, 21 pages. (Year: 2003).*
FAO (Year: 2003).*
Kuhre et al.(Year: 2014).*
Lin et al., Gastric Emptying of Solid Food Is Most Potently Inhibited by Carbohydrate in the Canine Distal Ileum, 1992, Gastroenterology, 102, 792-801. (Year: 1992).*
International Search Report and Written Opinion for Int'l Application No. PCT/EP2019/055792, titled: A Composition for Type II Diabetics and for Use in Providing Sustained Energy Release Over Time, Date Mailed: Jul. 24, 2019.
International Search Report and Written Opinion for Int'l Application No. PCT/EP2019/055791, titled: A Method Inducing Satiety in a Mammal, Date Mailed: Sep. 4, 2019.
International Preliminary Report on Patentability for Int'l Application No. PCT/EP2019/055791, titled: A Method Inducing Satiety in a Mammal, Date of Issuance: Sep. 8, 2020.
Alleleyn, A et al., "Gastrointestinal Nutrient Infusion Site and Eating Behavior: Evidence for a Proximal to Distal Gradient within the Small Intestine?" Nutrients, 8(3): 117 (Feb. 2016).
Alleleyn, A et al., "The Effect of an Encapsulated Nutrient Mixture on Food Intake and Satiety: A Double-Blind Randomized Cross-Over Proof of Concept Study," Nutrients, 10(11): 1787 (Nov. 2018).
Van Avesaat, M et al., "Ileal Brake Activation: Macronutrient-Specific Effects on Eating Behavior?" International Journal of Obesity, 39(2): 235-243 (Feb. 2015).
Yoder, S.M et al., "Stimulation of Incretin Secretion by Dietary Lipid: Is it Dose Dependent?" American Journal of Physiology - Gastrointestinal and Liver Physiology, 297(2): G299-G305 (Aug. 2009).

Non Final Office Action for U.S. Appl. No. 16/978,421 date mailed Jul. 28, 2023 (HBSR Docket No. 5867.1001-002(P12497USPC)).
Adrian TE, Long RG, Fuessl HS, Bloom SR. Plasma peptide YY (PYY) in dumping syndrome. Dig Dis Sci. 1985;30(12):1145-8.
Anal AK, Singh H. Recent advances in microencapsulation of probiotics for industrial applications and targeted delivery. Trends Food Sci Technol. 2007; 18(5):240-251.
Aponte, G.W. et al., "Primary culture of PPY cells from canine colon," Am J Physiol. 1988;254(6): G829-G836.
Batterham, R.L. et al., "Critical role for peptide YY in protein-mediated satiation and body-weight regulation," Cell Metabolism, vol. 4; 223-233 (2006).
Burns AA, Livingstone MB, Welch RW, Dunne A, Reid CA, Rowland IR. The effects of yoghurt containing a novel fat emulsion on energy and macronutrient intakes in non-overweight, overweight and obese subjects. Int J Obes Relat Metab Disord. 2001;25(10):1487-96.
Burns AA, Livingstone MB, Welch RW, Dunne A, Robson PJ, Lindmark L, Reid CA, Mullaney U, Rowland IR. Short-term effects of yoghurt containing a novel fat emulsion on energy and macronutrient intakes in non-obese subjects. Int J Obes Relat Metab Disord. 2000;24(11):1419-25.
Burns AA, Livingstone MB, Welch RW, Dunne A, Rowland IR. Dose-response effects of a novel fat emulsion (Olibra) on energy and macronutrient intakes up to 36 h post-consumption. Eur J Clin Nutr. 2002;56(4):368-77.
Chan YK, Strik CM, Budgett SC, McGill AT, Proctor J, Poppitt SD. The emulsified lipid Fabuless (Olibra) does not decrease food intake but suppresses appetite when consumed with yoghurt but not alone or with solid foods: a food effect study. Physiol Behav. 2012;105(3):742-8.
Choi CH, Jung JH, Rhee YW, Kim DP, Shim SE, Lee CS. Generation of monodisperse alginate microbeads and in situ encapsulation of cell in microfluidic device. Biomed Microdevices. 2007;9(6):855-62.
Diepvens, K. et al., "Short-term effects of a novel fat emulsion on appetite and food intake," Physiology & Behavior; vol. 95; 114-117 (2008).
Final Office Action received for U.S. Appl. No. 16/978,421, mailed on Apr. 12, 2024, 8 pages.
International Preliminary Report on Palenlability for Inl'l Application No. PCT/EP2019/055792, tilled: A Composition for Type II Diabetics and for Use in Providing Sustained Energy Release Over Time, Dale of Issuance: Sep. 8, 2020.
Lin HC, Zhao XT, Wang L, Wong H. Fat-induced ileal brake in the dog depends on peptide YY. Gastroenterology. 1996;110(5):1491-5.
Lin HC, Zhao XT, Wang L. Intestinal transit is more potently inhibited by fat in the distal (ileal brake) than in the proximal (jejunal brake) gut. Dig Dis Sci. 1997;42(1):19-25.
Logan CM, McCaffrey TA, Wallace JM, Robson PJ, Welch RW, Dunne A, Livingstone MB. Investigation of the medium-term effects of Olibra™ fat emulsion on food intake in non-obese subjects. Eur J Clin Nutr. 2006;60(9):1081-91.
Maljaars, P.W.J. et al., "Length and site of the small intestine exposed to fat influences hunger and food intake," British Journal of Nutrition, vol. 106; 1609-1615 (2011).
Minekus, M. et al., "A computer-controlled system to simulate conditions of the large intestine with peristaltic mixing, water absorption and absorption of fermentation products," Appl. Microbiol. Biotechnol., vol. 53; 108-114 (1999).
Minekus, M. et al., "A Standardised static in vitro digestion method suitable for food—an international consensus," Food Funct., vol. 5; 1113; 12 pages (2014).
Nazzaro F, Orlando P, Fratianni F, Coppola R. Microencapsulation in food science and biotechnology. Curr Opin Biotechnol. 2012;23(2):182-6.
Non-Final Office Action received for U.S. Appl. No. 16/978,421, Mailed on Jul. 28, 2023, 8 pages.
Pironi, L. et al., "Fat-Induced Ileal Brake in Humans: A Dose-Dependent Phenomenon Correlated to the Plasma Levels of Peptide YY," Gastroenterology, vol. 105; 733-739 (1993).
Ramadan, M. et al., "Risk of Dumping Syndrome after Sleeve Gastrectomy and Roux-en-Y Gastric Bypass: Early Results of a

(56) References Cited

OTHER PUBLICATIONS

Multicentre Prospective Study," Gastroenterology Research and Practice, vol. 2016, Article ID 2570237; 5 pages (2016).

Rudnicki M, Kuvshinoff BW, McFadden DW. Extrinsic neural contribution to ileal peptide YY (PYY) release. J Surg Res. 1992;52(6):591-5.

Schellekens, R.C.A. et al., "Oral ileocolonic drug delivery by the colopulse-system: A bioavailability study in healthy volunteers," Journal of Controlled release, vol. 146; 334-340 (2010).

Smit HJ, Keenan E, Kovacs EM, Wiseman SA, Peters HP, Mela DJ, Rogers PJ. No efficacy of processed Fabuless (Olibra) in suppressing appetite or food intake. Eur J Clin Nutr. 2011;65(1):81-6.

Spiller RC, Trotman IF, Higgins BE, Ghatei MA, Grimble GK, Lee YC, Bloom SR, Misiewicz JJ, Silk DB. The ileal brake—inhibition of jejunal motility after ileal fat perfusion in man. Gut. 1984;25(4):365-74.

Van Avesaat M, Ripken D, Hendriks HF, Masclee AA, Troost FJ. Small intestinal protein infusion in humans: evidence for a location-specific gradient in intestinal feedback on food intake and GI peptide release. Int J Obes (Lond). 2017;41(2):217-224.

Van Beek, A.P. et al., "Dumping syndrome after esophageal, gastric or bariatric surgery: pathophysiology, diagnosis, and management," Obesity, vol. 18; 68-85 (2017).

Van Citters GW, Lin HC. Ileal brake: neuropeptidergic control of intestinal transit. Curr Gastroenterol Rep. 2006;8(5):367-73.

Varum FJ, Hatton GB, Freire AC, Basit AW. A novel coating concept for ileo-colonic drug targeting: proof of concept in humans using scintigraphy. Eur J Pharm Biopharm. 2013;84(3):573-7.

Vincent RP, Ashrafian H, le Roux CW. Mechanisms of disease: the role of gastrointestinal hormones in appetite and obesity. Nat Clin Pract Gastroenterol Hepatol. 2008;5(5):268-77.

Welch IM, Sepple CP, Read NW. Comparisons of the effects on satiety and eating behaviour of infusion of lipid into the different regions of the small intestine. Gut. 1988;29(3):306-11.

Welch, I. et al., "Effect of Ileal and Intravenous Infusions of Fat Emulsions on Feeding and Satieety in Human Volunteers," Gastroenterology, vol. 89; 1293-1297 (1985).

Woltman T, Reidelberger R. Effects of duodenal and distal ileal infusions of glucose and oleic acid on meal patterns in rats. Am J Physiol. 1995;269(1):R7-14.

Non-Final Office Action received for U.S. Appl. No. 16/978,421, mailed on Oct. 28, 2024, 10 pages.

Final Office Action received for U.S. Appl. No. 16/978,421, mailed on Mar. 14, 2025, 10 pages.

Jens Juul Holst et al., Actions of glucagon-like peptide-1 receptor ligands in the gut, Br J Pharmacol. 2022, 727-742, 179.

Non-Final Office Action received for U.S. Appl. No. 16/978,421, mailed on Oct. 23, 2025, 12 pages.

* cited by examiner

| Time | Activity |
|------|----------|
| 08:00 | Subject Arrives fasted |
| 08:05 | Body Measurements |
| 08:10 | Fasting Visual Analogue Scale (VAS) |
| 08:15 | Baseline Blood draw |
| 08:20 | Consumption of Microparticulate Drink |
|       | (10 minutes) |
| 08:45 | VAS and Blood Draws 1 |
| 09:00 | VAS and Blood Draws 2 |
| 09:10 | Sensory Questionnaire |
| 09:30 | VAS and Blood Draws 3 |
| 10:00 | VAS and Blood Draws 4 |
| 10:30 | VAS and Blood Draws 5 |
| 11:00 | VAS and Blood Draws 6 |
| 11:30 | VAS and Blood Draws 7 |
| 11:35 | Ad Libitum meal |
| 11:55 | Subjects leaves |

FIGURE 1

| | |
|---|---|
| * | significant at 5 % |
| ** | significant at 1 % |
| *** | significant at 0,1 % |
| ! | test not computed |

Group 1
Group II

Chalky
Glue
Sweet ***
Salt *
Sour
Bitter
Mouthdrying
Mouthcoating **
Nutty *
Encapsulated **
Oatmeal
Green *
Bitter A/t *
Starch A/t *
Dairy ***
Length Flavour **
Starch

COMPOSITION FOR TYPE II DIABETICS AND FOR USE IN PROVIDING SUSTAINED ENERGY RELEASE OVER TIME

This application is the U.S. National Stage of International Application No. PCT/EP2019/055792, filed on Mar. 7, 2019, which designates the U.S., published in English, and claims priority under 35 U.S.C. § 119 or 365 (c) to European Application No. 18160601.3, filed on Mar. 7, 2018. The entire teachings of the above applications are incorporated herein by reference.

FIELD OF THE INVENTION

The present invention relates to a composition for use in providing sustained energy release over time and regulation of post-prandial blood sugar levels. Also contemplated are methods of delivering a high glycaemic index (GI) carbohydrate to the bloodstream of a mammal.

BACKGROUND TO THE INVENTION

The absorption profile of carbohydrates in the human gut depends on the type of carbohydrate involved, and in particular the glycaemic index (GI) value of the carbohydrate. Complex carbohydrates, such as are found in peas, beans, vegetables and whole grains have a low GI value (Index less than 55), as they have to be broken down in the human gut and therefore are absorbed in the bloodstream slowly providing sustained energy release without post-prandial peaks in blood sugar levels. In contrast, simple carbohydrates (i.e. monosaccharides and disaccharides) are absorbed into the blood stream quickly, resulting in spikes in blood sugar levels within 60-90 minutes of consumption. The body has to work hard to absorb and metabolise simple sugars so quickly, which leads to a feeling of tiredness in the subject. In subjects with certain metabolic disorders, especially those with dysregulated insulin production such a Type II diabetes, the spikes in blood sugar levels that are characteristic of consumption of high GI sugars can be extremely dangerous, as insufficient insulin is available to adequately metabolise the high blood sugar levels. Subjects with Type II diabetes therefore have to avoid high energy sugar products, and satisfy their energy needs using lower energy products, which can result in insufficient calorific intake.

It is an object of the invention to overcome at least one of the above-referenced problems.

SUMMARY OF THE INVENTION

The present invention addresses the need for a food product that contains high GI carbohydrate that is absorbed into the bloodstream in a sustained manner with attenuated post-prandial spikes in blood sugar levels. The sugar is contained within a gastric-resistant carrier configured for transit through the stomach of a mammal and ileal release. Data obtained by the applicant (FIGS. 3A-3B) shows that when sugars are protected during gastric transit and released in the ileum/distal bowel, the energy is released over time in a sustained manner and the spikes in blood sugar levels that occur with conventional sugar delivery are avoided, making the composition of the invention suitable for use by patients with metabolic disorders such as Type II diabetes or metabolic syndrome. In addition, the composition provides the energy content of a high GI sugar, with a release profile of low GI sugar, which allows for use by diabetic subjects who would otherwise have to avoid products containing high GI sugars. The composition may be taken as a meal replacement (and may include other nutritional components such as protein and fat), or it may be taken between meals to help regulate glucose levels between meals, or it may be taken with a meal including non-coated carbohydrates, where it helps attenuate spikes in blood sugar levels attributable to the non-coated carbohydrates. The coated high GI sugar is typically provided in the form of a microparticulate, and the microparticulate may have a core-shell morphology with a carbohydrate core contained within a gastric resistant, ileal-sensitive, shell, or may have a multinuclear morphology with pockets of carbohydrate dispersed throughout a continuous matrix. The composition may be a microparticulate powder, or a nutritional composition containing the microparticulate, for example a food or beverage. The composition may also be administered to an at-risk population (diabetics, pre-diabetics, obese subjects) to regulate post-prandial blood glucose levels in these subjects, or to increase sensitivity to insulin. Surprisingly, the Applicant has discovered that the microparticulate powder has a sweet taste, despite the sucrose being contained within a protective shell (FIG. 2).

According to a first aspect of the present invention, there is provided a composition for use in a method of regulating post-prandial blood sugar levels, the composition comprising carbohydrate contained within a gastric-resistant, ileal-sensitive, non-porous carrier configured for release of the carbohydrate in the distal ileum.

According to another aspect of the present invention, there is provided a composition for use in a method of inhibiting post-prandial spikes blood sugar levels, the composition comprising carbohydrate contained within a gastric-resistant, ileal-sensitive, non-porous carrier configured for release of the carbohydrate in the distal ileum.

According to another aspect of the present invention, there is provided a composition for use in a method of normalising blood glucose homeostasis, the composition comprising carbohydrate contained within a gastric-resistant, ileal-sensitive, non-porous carrier configured for release of the carbohydrate in the distal ileum.

According to another aspect of the present invention, there is provided a composition for use in a method of increasing sensitivity to insulin in a subject, especially a subject having a metabolic disorder characterised by dysregulated insulin production, the composition comprising carbohydrate contained within a gastric-resistant, ileal-sensitive, non-porous carrier configured for release of the carbohydrate in the distal ileum.

According to a further aspect of the invention, there is provided a method of delivering a high glycaemic index (GI) carbohydrate to the bloodstream of a mammal providing sustained energy release with attenuated spikes in post-prandial blood sugar levels, the method comprising the steps of:

providing a composition comprising the high GI carbohydrate contained within a gastric-resistant, ileal-sensitive, non-porous carrier configured for release of the carbohydrate in the distal ileum; and orally administering the composition to the mammal.

The composition may be a food, beverage, food supplement, food ingredient, or therapeutic or pharmaceutical product. The composition may be a powder.

In one embodiment, all or substantially all of the carbohydrate (i.e. at least 90% of the carbohydrate) in the composition is contained within the gastric-resistant, ileal-sensitive, non-porous carrier configured for release of the carbohydrate in the distal ileum.

In one embodiment, the carbohydrate contained within a gastric-resistant, ileal-sensitive, non-porous carrier is provided in as a microparticulate.

In one embodiment, the microparticles comprise a core and a non-porous shell micro-encapsulating the core, in which the core comprises or consists essentially of the carbohydrate (mononuclear morphology).

In one embodiment, the carrier is a matrix, and the carbohydrate is dispersed throughout the matrix (multinuclear).

In one embodiment, the carbohydrate is or comprises a high GI carbohydrate.

In one embodiment, the carbohydrate is in a solid form.

In one embodiment, the microencapsulate is formed by fluidised bed drying.

In one embodiment, the carbohydrate is in liquid form.

In one embodiment, the microencapsulate is formed by nozzle extrusion, preferably nozzle co-extrusion.

In one embodiment, the composition is provided in a unit dose form, in which the composition comprises 100 to 1000 Kcal of carbohydrate contained within the microparticles In one embodiment, the carbohydrate is selected from monosaccharide and disaccharide, or a combination thereof.

In one embodiment, the composition comprises an artificial sweetener.

In one embodiment, at least 90% of the carbohydrate in the composition is contained within a gastric-resistant, ileal-sensitive, non-porous shell configured for release of the carbohydrate in the distal ileum.

In one embodiment, the carrier comprises or consists essentially of polymerised protein. In one embodiment, the protein comprises denatured or hydrolysed protein. In one embodiment, the protein is selected from dairy or plant protein.

In one embodiment, the composition comprises protein and fat.

In one embodiment, the composition is a food ingredient powder. In one embodiment, the food ingredient powder is formed by nozzle extrusion or fluidised bed drying.

In one embodiment, the composition is a food or beverage product.

In one embodiment, at least 85% by weight of the microparticle is carbohydrate (typically high GI carbohydrate).

In one embodiment, the use is for regulating blood sugar levels in a subject with a metabolic disease such as diabetes.

In one embodiment, the composition is administered before a meal, for example 1-3 hours before a meal.

According to another aspect of the present invention, there is provided a use of a composition as a low GI food ingredient, in which the composition is a microparticulate powder in which the microparticles comprise high GI sugar contained within a gastric-resistant, ileal-sensitive, non-porous carrier configured for release of the carbohydrate in the distal ileum.

According to another aspect of the present invention, there is provided a method of making a microparticulate food ingredient, comprising the steps of:

drying a carbohydrate on a fluidised bed dryer; and simultaneously spraying a gastric-resistant, ileal-sensitive, coating material onto the carbohydrate material during drying.

In one embodiment, the coating material is a protein, typically a denatured or hydrolysed protein. In one embodiment, the protein is a dairy or vegetable protein.

In another aspect, the invention provides a composition of microparticles, in which the microparticles comprise a carbohydrate core contained within a gastric-resistant, ileal-sensitive, carrier configured for release of the carbohydrate in the ileum.

In one embodiment, the microparticles have a core-shell morphology comprising a carbohydrate core in which the carrier comprises a shell surrounding the core.

In one embodiment, the carrier is a matrix, and the carbohydrate is dispersed throughout the matrix (multinuclear).

In one embodiment, the carrier comprises a polymerised protein or shellac membrane.

In one embodiment, the protein is denatured or hydrolysed protein.

In one embodiment, the protein is dairy or plant protein.

In one embodiment, the composition comprises 100-1000 Kcal of carbohydrate, in which the carbohydrate is contained within the microparticles.

In one embodiment, the carbohydrate core consists essentially of carbohydrate.

In one embodiment, the carbohydrate is high glycaemic index carbohydrate.

In one embodiment, the protein is denatured or hydrolysed protein, and the lipid core consists essentially of lipid.

In one embodiment, the protein is denatured or hydrolysed protein, and the composition comprises 100-1000 Kcal of carbohydrate contained within the microparticles.

In one embodiment, the protein is denatured or hydrolysed plant or dairy protein, the carbohydrate core consists essentially of carbohydrate, and the composition comprises 100-1000 Kcal of carbohydrate, in which the carbohydrate is contained within the microparticles.

In one embodiment, the microparticles are produced by fluidised bed drying.

In one embodiment, the microparticles are produced by micro-nozzle co-extrusion.

In one embodiment, the microparticles have an average dimension of less than 500 microns as determined by laser diffractometry.

In one embodiment, the microparticles have an average dimension of less than 200 microns as determined by laser diffractometry.

In one embodiment, the composition is a unit dose composition (for example, a capsule or tablet, or sachet).

In one embodiment, the microparticles are dried.

In another aspect, the invention provides a method of producing a composition of microparticles comprising a carbohydrate core contained within a gastric-resistant, ileal-sensitive, carrier configured for release of the carbohydrate in the ileum, and in which the carrier preferably comprises a polymerised membrane formed by denatured or hydrolysed protein or Shellac.

In one embodiment, the method employs a dual concentric nozzle extruder having an inner nozzle and an outer nozzle concentrically arranged around the inner nozzle, the method comprising the steps of simultaneously extruding carbohydrate through the inner nozzle and a denatured or hydrolysed protein dispersion (or shellac) through the outer nozzle to form microdroplets, and polymerising the microdroplets in a polymerisation bath to form microparticles, and optionally drying the microparticles.

In another embodiment, the method comprising the steps of providing:

solid carbohydrate microparticles on a fluidised bed, spraying a protein solution (i.e. 5-15% w/v) onto the bed to coat the carbohydrate particles and form microparticles, and drying the microparticles.

In one embodiment, a second protein solution (5-15% w/v) is sprayed on to the dried microparticles. In one embodiment, the second protein solution comprises protein in a weakly acidic buffer.

In one embodiment, the microparticles are produced by treating a liquid formulation by atomization via extrusion at elevated pressure through a nozzle under elevated temperature conditions to generate microcapsules comprising essentially a lipid core. Other aspects and preferred embodiments of the invention are defined and described in the other claims set out below.

BRIEF DESCRIPTION OF THE FIGURES

FIG. 1: Timeline of the test days. A test drink (microparticulate material or control) was ingested after body composition analysis and fasting. Blood samples, Visual Analogue Scale (VAS) scores were collected at several time points as indicated in the table. Glucose and insulin concentrations in blood plasma were measured. The ad libitum meal was administered 3 h after administration of microparticulated carbohydrate.

Figure 3A:
FIG. 3A: Mean±SEM plasma glucose concentration during the period after ingestion of the microparticulated drink (180 min). AUC's were calculated using the trapezoid rule. A significant difference was observed in plasma glucose concentration after ingestion of the microparticulated carbohydrate targeted for release in the stomach relative to microparticulated carbohydrate targeted for release in distal ileum/bowel, (n=76) P<0.0001. AUC, area under the curve.

Due to greater carbohydrate absorptive capacity in the proximal gut, insulin levels increase in the control group to a greater extent. Even with this increase a blood euglycemic concentration cannot be maintained in the control group (FIG. 3B). Microencapsulated material demonstrates lower overall insulin concentration yet maintains a euglycemic range FIG. 3).

Figure 5:
Figure 5:
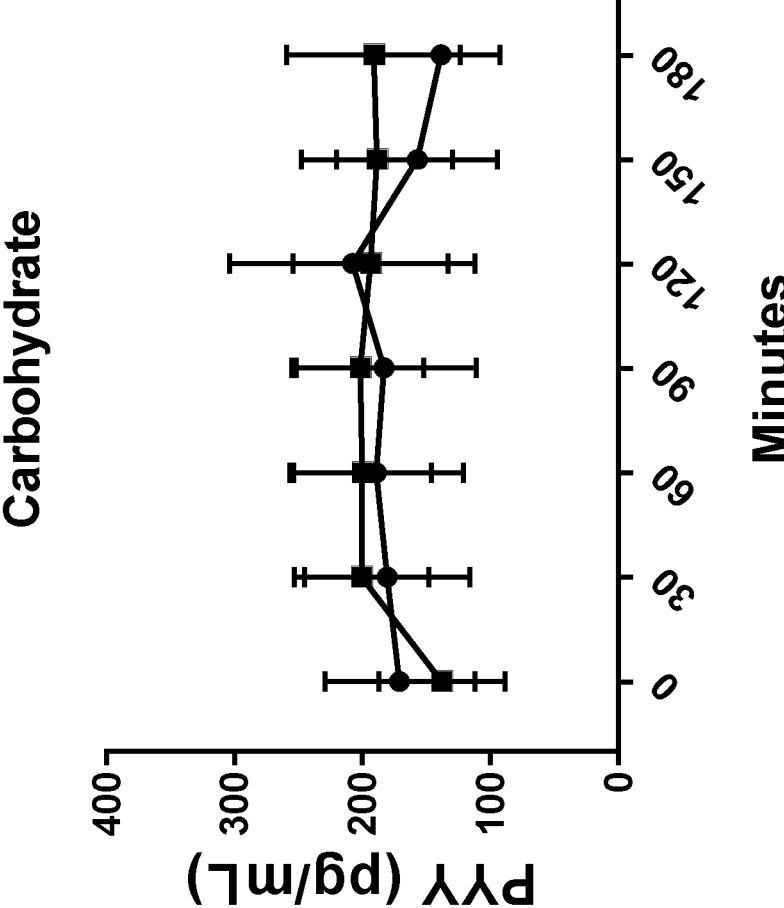

FIG. 5. Three hours AUC total plasma PYY measured during the period after ingestion of the microparticulated test drink (scheduled from 0 to 180 min) containing carbohydrate microparticulates released in the stomach relative to carbohydrate microparticulates released in the distal bowel. PYY is measured as pg/mL.

Figure 6:
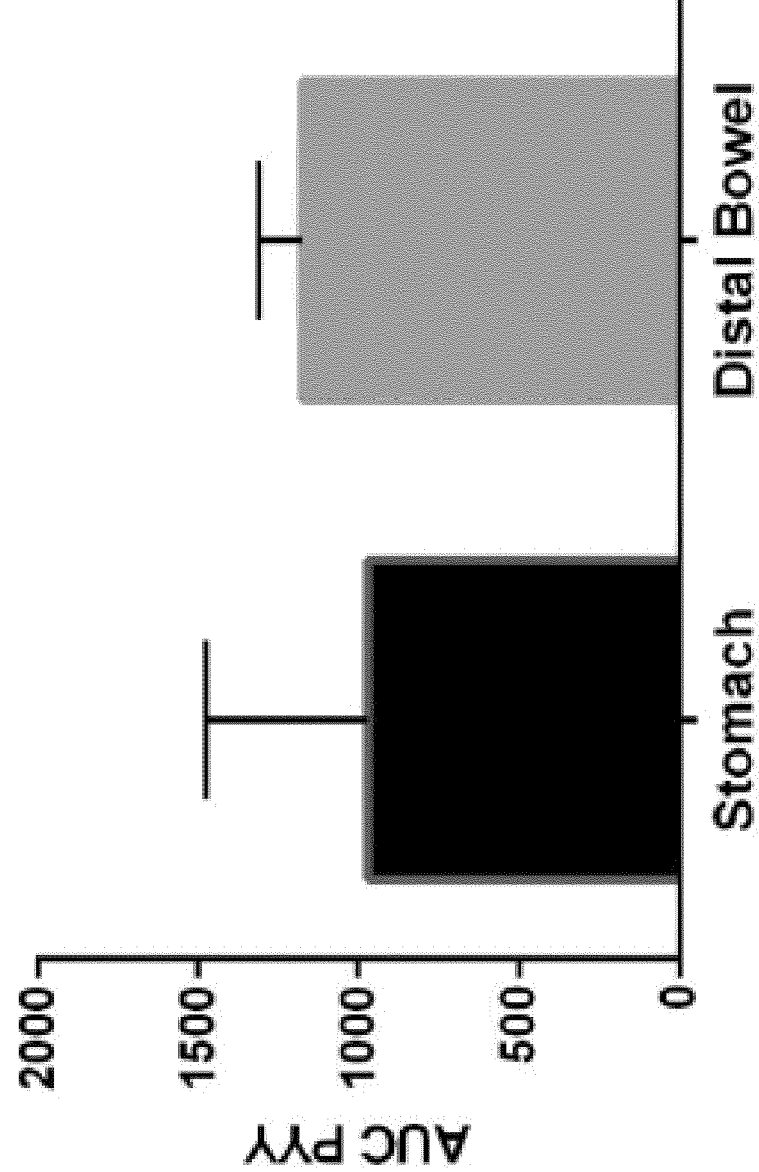

FIG. 6. AUC total plasma PYY concentration after administration of carbohydrate (T=0) microparticulates targeted for release (n=8) in the stomach and administration of carbohydrate microparticulates targeted for release distal bowel.

Figure 7:
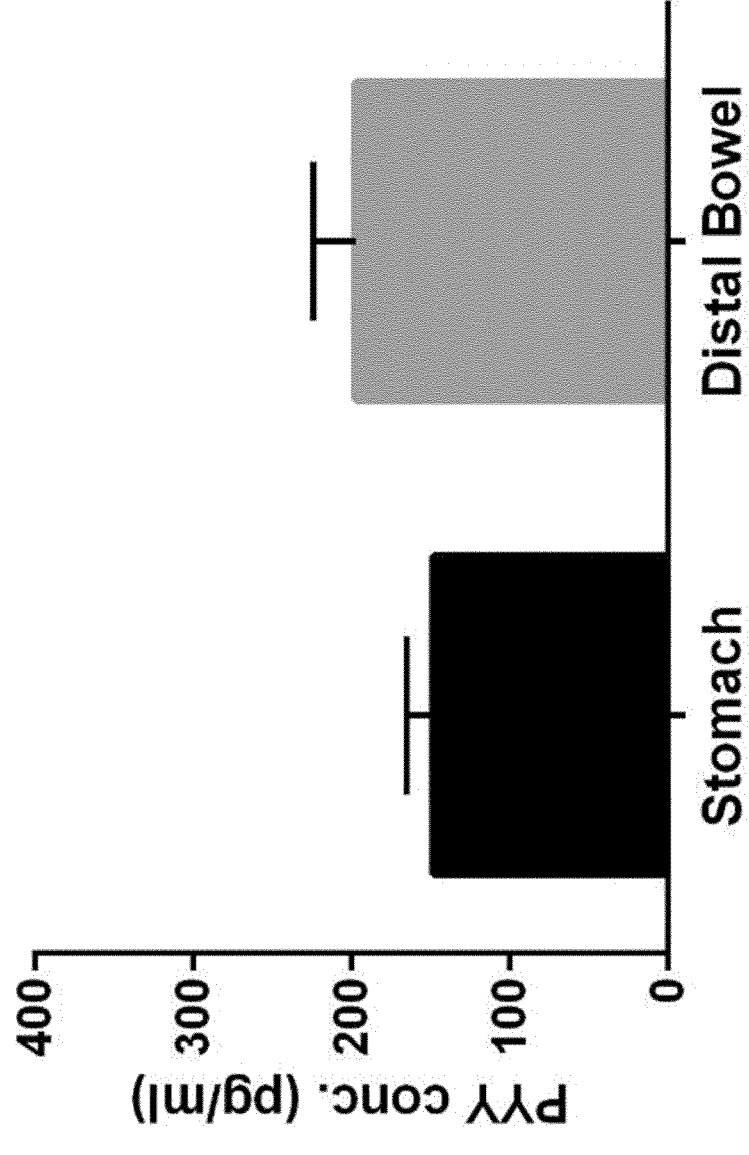

FIG. 7. PYY plasma concentration (pg/ml) at 180 mins for carbohydrate microparticulates (n=8) released in the stomach relative to carbohydrate microparticulates released in the distal bowel. Total plasma PYY levels were measured by ELISA analysis. Results are expressed as mean±SEM.

Figures 8A, 8B, 8C:
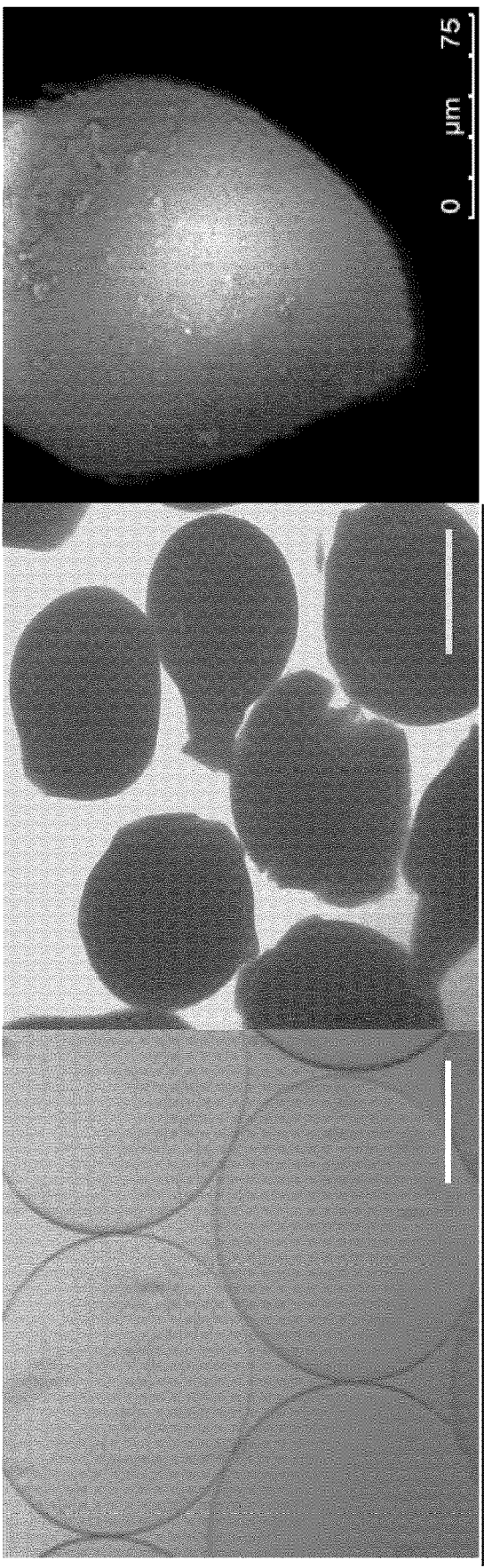

FIGS. 8A and 8B Light microscope image of a carbohydrate microparticulates of different sizes generated from a co-extrusion micro-nozzle encapsulation method; bars represents 50 microns. FIG. 8C illustrates the non-porous outer shell of a dry carbohydrate microparticulate that protects against gastric and other stress environments.

Figure 9A:
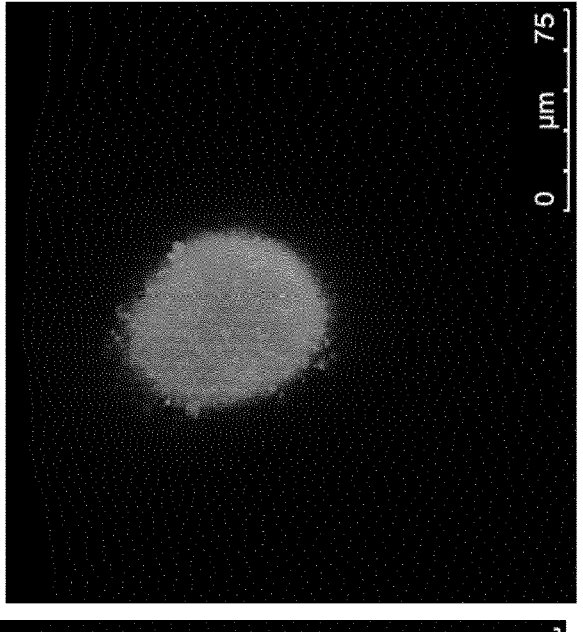
Figure 9B:
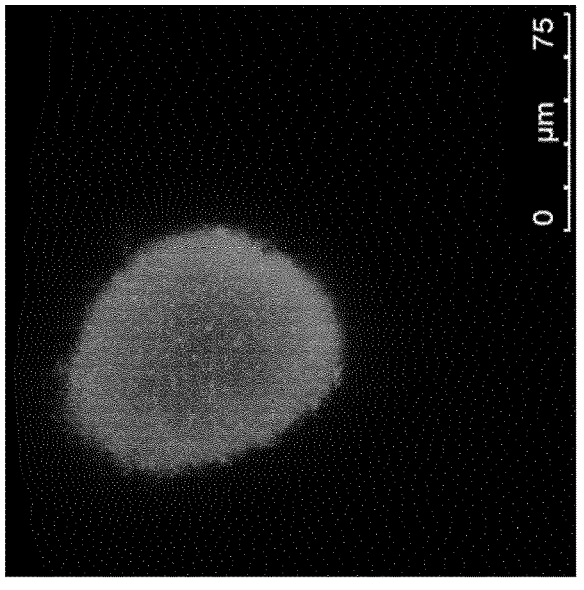
Figure 9C:
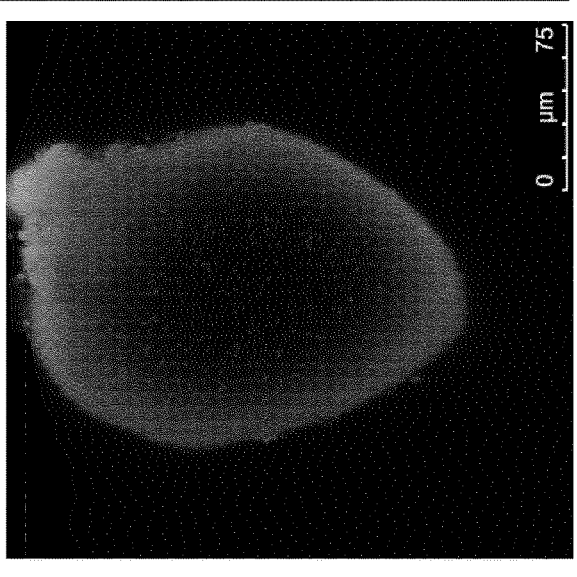

FIG. 9 shows Confocal Laser Scanning Microscope image (CLSM) image of carbohydrate microparticulates of different sizes and morphologies generated from fluidised bed technologies (A) and co-extrusion and fluid encapsulation methodologies (B and C). Fluorescent dyes (Nile Red and Fast Green) were used to distinguish between protein can carbohydrate components.

Figure 10:
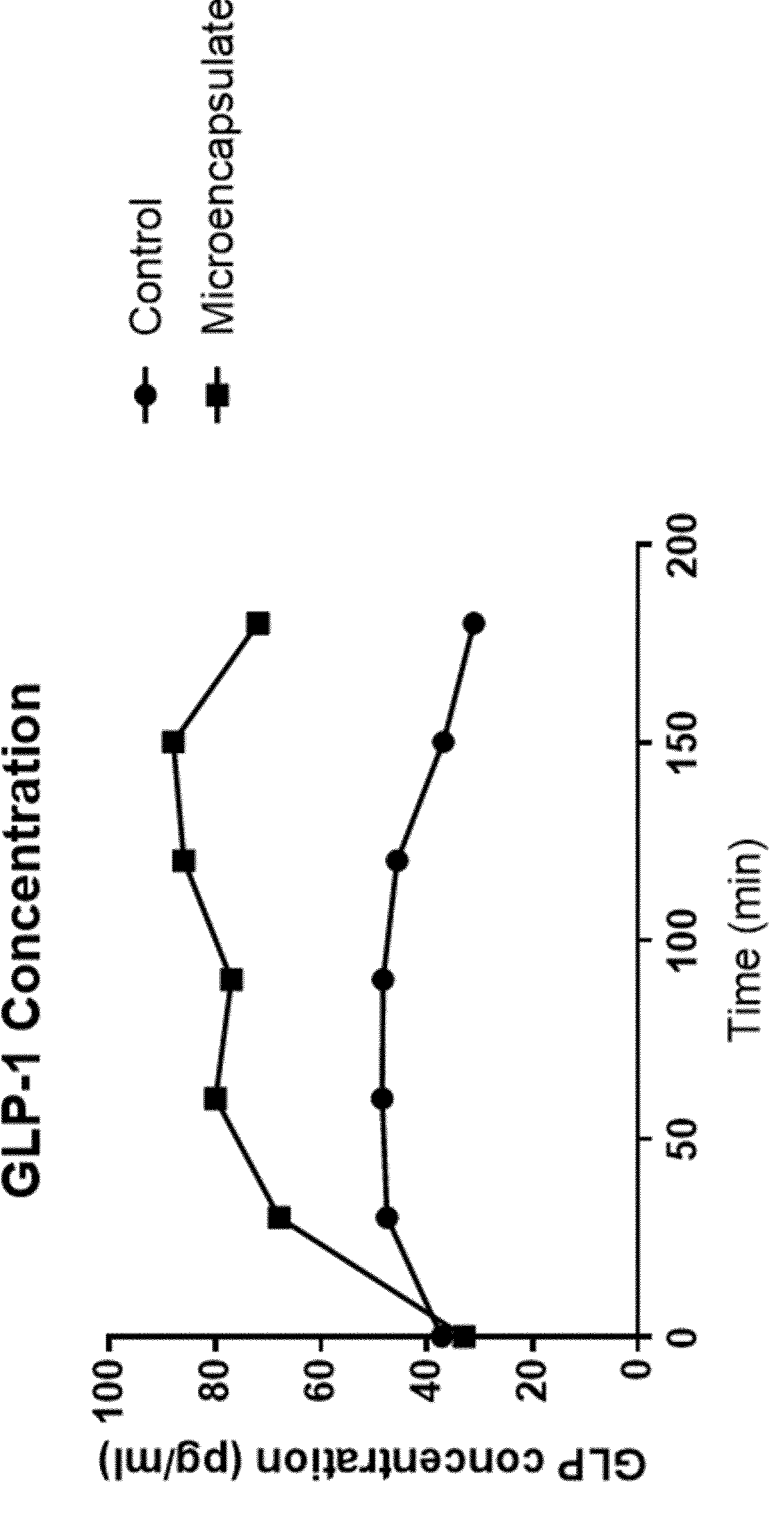

FIG. 10 shows Glucagon-like peptide-1 (GLP-1) concentration in the blood following ingestion of microencapsulated carbohydrate mixture in comparison to control ingredient. GLP-1 likely remains higher in the microencapsulated formulation due to dissolution and release in the ileum, which is the primary site for GLP-1 producing L-cell.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "metabolic disorder characterised by dysregulated insulin production" refers to Type II diabetes, pre-diabetes, obesity, inflammatory disorders, metabolic syndrome, immune-metabolic dysfunction, endoplasmic reticulum stress, inflammasome activation and pathogenesis.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy".

As used herein, the term "sensory analysis" is the study of the reactions of the five senses (sight, hearing, smell, taste and touch), specifically taste to the characteristics of carbohydrate microparticulated matter. The analysis does not just deal with "likes and dislikes," for the composition but scientifically measures, analyses and interprets psychological responses to physical stimuli, and thus belongs to the specialized field of psychophysics. In this case, the term is used synonymously with the term "Sweet". In preferred embodiments, the subject is a human.

As used herein, the term, "stimulus error" occurs when study participants are influenced by some characteristics of the sample (i.e. size, shape, colour, etc). In this case, the term is used synonymously with the term "stimulus". In preferred embodiments, the subject is a human.

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "regulating" as applied to post-prandial blood sugar levels means providing sustained energy release over time and/or attenuation or inhibition of spikes in post-prandial blood sugar level compared to a conventional composition containing the same type and amount of carbohydrate in which the carbohydrate is not protected from gastric or ileal release. The composition of the invention provides the high GI carbohydrate (or some of the carbohydrate) in a micro-encapsulated or protected form configured to contain the carbohydrate during transit and protection through the stomach and release of the full carbohydrate load in the ileum. The data contained herein shows that when the carbohydrate is released in the ileum, the level of increase in blood sugar levels is attenuated as a result of slow and prolonged absorption of carbohydrate in the ileum, providing more sustained energy release. This is especially suitable for certain subjects for whom spikes in blood sugars are dangerous, for example subjects with Type II diabetes and also subjects classed as pre-diabetic, for example subjects with metabolic syndrome, overweight/obese subjects, or subjects with cardiovascular disease, inflammatory disorders, metabolic syndrome, immune-metabolic dysfunction or endoplasmic reticulum stress. Thus, the use of the invention helps prevent, or attenuate, spikes in blood sugar levels, create glucose homeostasis and in particular help normalise post-prandial blood sugar levels to a reference level in a normal healthy subject. In one embodiment, the composition of the invention is used to normalise blood sugar levels within 30 minutes after a meal comprising the composition to under 180 mg/dl, 170 mg/dl, 160 mg/dl, 150 mg/dl, or 150 mg/dl.

As used herein, the term "normalising blood glucose homeostasis" means promoting a balance of insulin and glucagon in a subject that helps maintain blood glucose at a level of a healthy subject.

As used herein, the term "post-prandial" as applied to blood sugar levels means a 15 min-2-hour period after consumption of the composition, or in the case of administration of the composition 1-3 hours before a meal, a period of time (i.e. 1-2 hours) after consumption of the meal. The composition of the invention helps provide sustained energy release from a high GI sugar, and attenuate, inhibit or avoid post-prandial spikes in blood sugar levels compared with consumption of an equal amount of the same carbohydrate that is not fully protected from gastric release.

As used herein, the term "composition" refers to a composition suitable for oral administration and includes foods, beverages, food supplements, food ingredients (for example powders comprising microparticulates), therapeutic and pharmaceutical compositions. The composition comprises or consists of high GI carbohydrate contained within a gastric-resistant, and ileal-sensitive, shell.

As used herein, the term "microparticle" or "microparticulate" refers to particulates having an average dimension of less than 1000 microns that contains carbohydrate protected from gastric release by an outer non-porous carrier configured for ileal release. The microparticles may have a mononuclear or multinuclear morphology. The microparticulates may be formed by a number of different methods, including fluidised bed drying methods and micro-nozzle extrusion methods. Micro-nozzle extrusion methods are described in the literature, and generally employ micro-extrusion of micro-beads through a suitable extruder and then solidification of the micro-beads in a suitable buffer bath, for example a bath containing an acidic buffer, ascorbate or calcium buffer. A single micro-nozzle system may be employed, where the carbohydrate and shell forming material (i.e. denatured or hydrolysed protein) are provided as a single suspension which is extruded through an extruder to form micro-droplets which are solidified in a solidification bath, and then dried. Such microparticulates generally have a solid matrix of, e.g. denatured or polymerised protein, and pockets of carbohydrate dispersed throughout the matrix. Alternatively, a double micro-nozzle system may be employed in which a carbohydrate is micro extruded from a central micro nozzle, and the shell forming material may be micro extruded through an outer, concentric, micro nozzle, forming droplets having a carbohydrate core micro-encapsulated within an outer shell (micro-nozzle co-extrusion). The microdroplets are then solidified within a gelling bath. Extrusion micro methods of forming microparticulates are described in WO2010/119041, WO2014/198787, WP2016/096929, WO2016/178202, and WO2016/185053. Generally, the methods are referred to herein as "extrusion methods" or "micronozzle extrusion methods". The microparticulates may also be formed by other, non-nozzle extrusion methods, for example by means of spray coating in a fluidised bed system (aka fluidised bed drying) described below, the details of which will be known to a person skilled in the art and described in the literature, for example (Anal, A., et al., 2007. Recent advances in microencapsulation of probiotics for industrial applications and targeted delivery. Trends in food Science and Technology, Volume 18, Issue 5, pg. 240-251) (Nazzaro, F., et al., 2012. Microencapsulation in food science and biotechnology, Current Opinion in Biotechnology, Volume 23, Issue 2, 2012, pg 182-186). In these embodiments, each microparticulate may comprise an agglomerate of small microparticulates, and the core is generally solid. An essential part of the process employed to produce the microparticulate is that the core is protected by an outer shell (coating) that is non-porous, gastric resistant and capable of ileal release. In one embodiment, the microparticles are produced by treating a liquid formulation by atomization via extrusion at elevated pressure through a nozzle under elevated temperature conditions to generate microcapsules comprising essentially a lipid core. In the embodiments described below, the Applicant has employed heat-treated protein for this purpose (for example, denatured milk, casein or whey protein), although other coating materials may be employed that are suitable for gastric protection and ileal release. In a preferred embodiment of the invention, the coating is a protein material, especially a milk or plant protein. In one embodiment of the invention, the microparticulates or microcapsules are dried.

As used herein, the term "gastric-resistant" as applied to the composition (or the microparticulate contained within the composition) means that the composition or microparticulate can survive intact for at least 60-120 minutes in the simulated stomach digestion model described in Minekus et al., 1999 and 2014 (A computer-controlled system to simulate conditions of the large intestine with peristaltic mixing, water absorption and absorption of fermentation product, Minekus, M., Smeets-Peeters M, Bernalier A, Marol-Bonnin S, Havenaar R, Marteau P, Alric M, Fonty G, Huis in't Veld J H, Applied Microbiology Biotechnology. 1999 December; 53 (1):108-14) and (Minekus et al., 2014, A standardised static in vitro digestion method suitable for food—an international consensus, Minekus, A. et al., Food Function, 2014, 5, 1113).

As used herein, the term "ileal-sensitive" as applied to the composition (or the microparticulate contained within the composition) means that the composition or microparticulate are capable of releasing their contents in vivo in the ileum of a mammal.

As used herein, the term "coating material" or "carrier material" refers to material that is GRAS status and is capable of forming a carrier, for example a shell or coating around carbohydrate and is gastric-resistant and capable of ileal release. In a preferred embodiment, the coating material is protein, preferably a dairy or vegetable protein. In one embodiment, the protein is denatured or hydrolysed protein. In one embodiment, the dairy protein is selected from milk protein concentrate, whey protein concentrate, whey protein isolate, and a caseinate, for example sodium caseinate or calcium caseinate. The vegetable protein may be a protein derived from pea, egg, wheat or rice, or any combination thereof. The protein may be in the form of a concentrate or an isolate. In one embodiment, the coating material may be an enteric coating material commonly employed in the pharmaceutical industry; examples include methyl-(meth) acrylate-methacrylic acid copolymers, cellulose acetate phthalate, cellulose acetate succinate, gelatin, sodium alginate, and shellac.

As used herein, the term "denatured" as applied to protein refers to means partially or fully denatured. Preferably at least 90%, 95% or 99% of the protein is denatured. A method of determining the % of denatured protein is provided below.

As used herein, the term "polymerised" as applied to protein means that the protein is polymerized or crosslinked, for example as a result of cold-gelation in a gelling bath or fluidised bed drying. Preferably, the polymerized protein forms a water or fluid impermeable shell.

As used herein, the term "hydrolysed" as applied to a protein means that the protein has been treated to at least partially digest native protein, in one embodiment treated with a protease enzyme composition. Suitably, the hydrolysed protein has a degree of hydrolysis (% DH) of 18-85%. Degree of hydrolysis (DH) is defined as the proportion of cleaved peptide bonds in a protein hydrolysate, and is determined using the OPA spectrophotometric assay, which involve the using N-acetyl-L-Cysteine (NAC) as the thiol reagent.

As used herein, the term "high GI carbohydrate" refers to sugars having a high glycaemic index (i.e. Index greater than 55). Examples include monosaccharides and disaccharides. The disaccharide may be sucrose, maltose, trehalose or the like. Preferably, the disaccharide is sucrose or maltose. The monosaccharide may be glucose, fructose or galactose. In a preferred embodiment, the high GI carbohydrate is sucrose.

As used herein, the term "distal ileum" or "distal bowel" refer to the part of the small intestine that intersects with the large intestine. It contains the ileocecal sphincter, a smooth muscle sphincter that controls the flow of chyme into the large intestine. The distal ileum is the distal segment of small bowel. It immediately precedes the small bowel's connection with the colon through the ileocaecal valve. While the small intestine is well characterised for its roles in the digestion and absorption of nutrients, it mediates another important role in its ability to sense the presence of nutrients in the gut lumen.

As used herein, the term "unit dose" as applied to a composition refers to an amount of the composition that contains 10-3000, 10-200, or 10-1000 Kcal of carbohydrate. The unit dose may be a beverage or a food product, beverage, capsule, pill, sachet, or the like.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Materials and Methods

The study was approved by the Medical Ethics Committee and was conducted in full accordance with the principles of the Declaration of Helsinki of 1975 as amended in 2013, and approval from the Irish and European Medical Research Committee. All participants gave written informed consent before participation. This trial was registered at www.clinicaltrials.gov as required.

Participants

Power analysis was performed and 8 and 76 healthy volunteers were recruited for two respective trials. Volunteers were recruited by local advertisements and posters outlining the study initiative were placed in public areas such as hospital waiting rooms, with contact information. Social media websites such as Twitter were also used to advertise. Advertisements only contained essential information relating to the study and contact details as approved by the ethics committee. Potential participants identified through these methods were thus able to contact the research investigator, after which they received written information providing further details about the study and were invited to attend a screening visit.

Screening

Screening visits took place at the Clinical Research Centre. Volunteers were fully informed on what the study entailed and any risks involved in participating. They were made aware that they reserved the right to withdraw at any given time during the study and that their data would not be used if they did so. Participants were given the Participant Information Sheet to read and had the opportunity to raise any questions or concerns.

After providing initial information, detailed study information was provided to all interested volunteers. Written informed consent was obtained after an interval of at least 14 days.

At this point, if participants were satisfied to proceed, consent was obtained and their eligibility was further assessed according to the inclusion and exclusion criteria. Inclusion criteria included age 18-50 years, normal fasting glucose, a body mass index (BMI) between 25 and 30 kg/m².

It was necessary to exclude individuals with metabolic dysfunction or any other condition or comorbidity that may have compromised compliance rates and ability to participate, such as diabetes, obesity, smoking, substance abuse, pregnancy, use of medications, and chronic illness. All participants reported to have a weight stable for min. 1 month before screening and unrestrained eaters or dieters were excluded from the study.

Study Design

This double-blind, randomized, controlled crossover study compared the effect of a microparticulated carbohydrate (within a protein matrix) targeting the distal ileum with that of an identical control containing microparticulated carbohydrate (within an alginate system) with subsequent disintegration in the stomach.

Each of the subjects were assigned a study code and randomised to receive each microparticulate preparations in their successive visits (either carbohydrate microparticulate targeted for stomach or distal ileum).

Study Products

The carbohydrate microparticulates designed for release in the distal bowel were generate using one of two methods:

METHOD 1: Co-extrusion production of powdered carbohydrate micro-capsules

METHOD 2: Fluidised bed production of powder carbohydrate microparticulates

Method 1:

Generation of Micro-Capsules

The micro-encapsulation system entraps sucrose to generate micron-sized micro-capsules for controlled delivery of native sucrose to the distal bowel. Carbohydrate micro-capsules were produced according to GMP guidelines (Bleiel S, inventor Gastro-resistant microencapsulates, and uses thereof to stimulate in-vivo ileal GLP-1 release in mammal. Ireland 2016 23 Jun. 2016). A highly concentrated solution of sucrose was prepared and co-extruded through a micron-concentric nozzle apparatus. The outer nozzle containing denatured whey protein was concentrically arranged around an inner nozzle containing the sucrose load. This enables the extrusion of the denatured whey protein through the outer nozzle and sucrose was co-extruded in the inner nozzle. Flow rates were managed precisely to enable consistent flow of outer and inner fluids.

Generation of a Steady Jet Stream

It is important to manage efficient jet stream generation (prevent coalescence of the droplets) before the fluids reach the polymerisation bath. To prevent coalescence of the droplets, which results in loss of mono-dispersity and an increase in the standard size deviation of the resulting micro-capsules, Coulomb forces were exploited to generate a stable jet stream. The magnitude of the Coulomb force has an important effect on efficiency of encapsulation since high kV values can have a deleterious effect on carbohydrate loads and cause leakage of the core material due to enlargement of pores.

Generation of Polymerisation Buffer

An acidic buffer, such as sodium acetate can be prepared as outlined in (Bleiel S, inventor Gastro-resistant microencapsulates, and uses thereof to stimulate in-vivo ileal GLP-1 release in mammal. Ireland 2016 23 Jun. 2016). Alternatively, an ascorbate buffer can be prepared using Na-Acetate and Ascorbic Acid. Molarity can be equilibrated at 0.4M-0.6M, pH 4.4-5.0, in order to ensure efficient encapsulation and polymerisation effects.

Importance of Electrophoretic Mobility

Electrophoretic mobility is used to determine both attractive and repulsive features of carbohydrate and protein matrix ingredients within the micro-capsule. The magnitude of interactions will identify the optimum electrostatic potential for stable micro-capsule storage. The electrical properties of sucrose were evaluated by micro-electrophoresis. The electrophoretic mobility (EM) of the carbohydrate load and protein coating was evaluated using the Helmholtz-Smoluchowski equation. Data has indicated that a very strong protein/carbohydrate interaction occurs between pH 3.0-6.0, hence an acid polymerisation bath was used to generate these micro-capsules.

Micro-Capsule Production Process

The recommended micro-bead production process temperature is 25-35° C. encapsulation of carbohydrate loads. Higher temperatures especially in combination with turbulence, can lead to increased loss of the carbohydrate inner material.

Method 2:

Generation of Microparticulates

The microparticulate system also englobes sucrose to generate micron-sized particulates for controlled delivery of native sucrose to the distal bowel. Carbohydrate microparticulates were produced according to GMP guidelines using similar solutions as outlined above i.e. Heat-treated whey protein (18% dry matter) was first admixed with an acidic buffer, (0.5M). This solution was then agitated at 35° C. to allow air pocket to evacuate, and then extruded through a spray micro-nozzle onto a bed of (dry) sucrose particles. Once a moisture content of 8% was achieved, the coated sucrose particulates would further spray with heat-treated whey protein (10% dry matter). During this second process step a weak acidic buffer, (0.25 M) was blended with the heat-treated whey protein in order to ensure efficient encapsulation and polymerisation effects on the second coating layer. This further supports the non-porous microparticulate coating generated. This process generates a double-coating layer of the denatured whey protein on the sucrose. These carbohydrate microparticulates are equally robust and protective for the delivery of sucrose to the distal bowel.

Micro-Particulate Production Process

The recommended fluidised production process temperature is 37-39° C. for encapsulation of carbohydrate loads. Zeta potential was also used to determine both attractive and repulsive features of carbohydrate and matrix protein ingredients within each process step i.e. first coating and secondary coating.

The carbohydrate microparticulate drink was prepared using material generated from Method 1 and Method 2. Data presented in FIGS. 3A and 3B confirm that a glucose plasma regulatory response can be generated with either production method. There is no significant difference identified in the results using material from either methods.

Carbohydrate microparticulate drinks were prepared using two kcal contents: 150 kcal and 500 kcal. Testing of both kcal loads showed no significant difference in the glucose regulatory effect on blood plasma.

The control test drink is designed for carbohydrate delivery to the stomach and it contained the same energy density (150 kcal or 500 kcal) and carbohydrate content as the carbohydrate microparticulate drink. Ca-alginate microbeads were prepared using GMP procedures, using 1.5% w/v sodium alginate and the crosslinking agent was calcium chloride (0.5 M). The material was prepared as per the Choi et al 2007 reference (Choi, C H., et al 2007. *Generation of monodisperse alginate microbeads and in situ encapsulation of cell in microfluidic device. Biomedical devices*, Volume 9, *issue* 6, pg 855-62) and the material was vacuumed dried. Residual content of calcium and chloride was tested to ensure a food-grade quality of the material.

For each study, dry powders of the carbohydrate microparticulate drink and control drink were prepared for each visit by weighing the appropriate amount to give a total calorific value of either i) 150 kcal or ii) 500 kcal for both carbohydrate microparticulate and control drinks.

Protocol

On the day before testing, subjects were instructed to abstain from heavy exercise and consumption of alcoholic beverages and to consume the same habitual meal as per their normal diet and routine. Participants were allowed to have water and this was measured.

The carbohydrate microparticulate and control drinks were prepared by an independent technician and offered to the participant in white bottles to blind both the investigator and the participant. All materials were produced according to GMP guidelines, utilising clean-label, food-grade sources of carbohydrate. Upon arrival in the lab on each test day, an intravenous cannula was placed in a forearm vein of the participant for collection of blood samples.

Shoes were removed for weight and height measurements. Height was measured to the nearest 0.1 cm using a stadiometer, on the first visit only. Subjects were weighed on a digital equilibrated scale, to the nearest 0.1 kg. Waist circumference was measured in the horizontal plane to the nearest 0.5 cm using non-stretchable measuring tape.

The fasting visual analogue scale (VAS) hunger score and the baseline blood draw were taken, and the subjects then received a 150 kcal or 500 kcal drink consisting of one of the microparticulate materials diluted in water and "zero calorie" Miwadi squash flavouring. The total volume varied based on the texture of each drink, which depended on the macronutrient base. Participants were allowed 10 minutes to consume the drink.

Fasted blood samples were taken and analysis was conducted as per FIG. 1. The participant ingested the carbohydrate microparticulate drink or control drink in randomized order on different test days (t=0 min).

At 15 min after the intake of the carbohydrate microparticulated drink or the control drink, blood draws were initiated A series of seven blood samples were then taken, first at 15 min, thereafter, 6 blood draws thereafter at 30 minute intervals. One plasma sample and one serum sample were taken using the respective Vacutainer® tubes, with a total volume of 10 mL of blood drawn per timepoint (inclusive of the fasted state. All subjects were asked to rate the taste Sensory Analysis Participants were asked to complete a Sensory Questionnaire with questions related to the taste, mouth feel and after-taste experienced from i) carbohydrate microparticulate drink or ii) identical carbohydrate load in free form in the same drink liquid. Success will be classified as no significant difference between the carbohydrate microparticulate drink and free carbohydrate (similar sucrose load) as consumed in the same beverage format. Furthermore, success was classified by the presence of any remarks related to "sweet note" or "sugar aftertaste" by the participants.

Stimulus error was avoided in the study by giving no information to the participants relating to the content of the drink and also by providing the drinks in white bottles.

After the final blood draw, participants were offered a standardised ad libitum meal to measure their food intake. This meal was selected from a choice of four isocaloric options (chicken korma; sweet chilli chicken; pasta bake; chicken tikka masala) at the beginning of the study, and the same meal was received at each visit. No technology was permitted during the meal and the participants ate in isolation to remove social influences.

The subjects were instructed to eat until they felt comfortably full and to remain for 20 min irrespective of when they finished eating, after which they could go home. The amount of food consumed was quantified by weighing the food before and after consumption, and the caloric intake was subsequently calculated.

Characterization of Micro-Encapsulates

Size Distribution and Drying Effects

Using light microscopy, wet micro-capsules recorded diameters of approx. 250 mm with a narrow range size distribution (±1.2 μm). Laser diffractometry was also incorporated and confirmed a D (v, 0.9) values for micro-encapsulates, revealing a diameter of 253.3±1.33 μm and 63.42±0.90 μm, pre- and post-drying respectively.

Stomach Incubation and Strength of Micro-Encapsulates

Strength of micro-capsule was analysed as a function of gastric incubation time in vivo (pH 1.2-1.4; 37° C.). No difference in micro-bead strength was reported for stomach incubation and enzyme-activated stomach conditions did not significantly (p, 0.01) weakened micro-bead strength. Tensile strength of micro-encapsulated carbohydrates remained unchanged with no reported leakage or loss of encapsulated carbohydrate. After 180 min gastric incubation, micro-particulates of carbohydrate maintained high tensile strength 119.23±2.14 nN, 6913±0.91 nN and 78.37±1.21 nN, respectively.

Intestinal Incubation and Degradation

Carbohydrate microparticulates were tested for intestinal delivery during in vivo transit trials. The maintenance of microparticulates containing carbohydrates integrity in the duodenum 48 minutes after oral ingestion of micro-encapsulates was tested and degradation was not evident.

Plasma was separated immediately by centrifugation (3,000×g) at 4° C. for 10 min and then stored at −20° C. until analysis.

Commercially available ELISA kits (Merck KGaA, Darmstadt, Germany; Cat. #EZHPYYT66K) were used to quantify total human PYY levels. The samples were thawed for 30 min prior to ELISA analysis. All samples were analysed together on 96-well plates to control for variation in temperature and day-to-day error. One kit was sufficient to measure 38 unknown samples in duplicate.

This was a sandwich ELISA assay, whereby total human PYY in the sample, encompassing both PYY1-226 and PYY3-36, bound to rabbit anti-human PYY IgG to form a complex. The wells of the microtiter plate were pre-coated with anti-rabbit IgG antibodies, and the complex therefore became immobilised to the plate. A biotinylated antibody then bound to the PYY, and unbound materials were washed away. The enzyme, horseradish peroxidase, was added and conjugated to the immobilised biotinylated antibodies. Free enzyme was washed away and immobilised antibody-enzyme conjugates were quantified by measuring enzyme activity upon addition of the substrate, 3,3',5,5'-tetra-methylbenzidine.

Following acidification of the products formed, the enzyme activity was measured spectrophotometrically (CLARIOstar™ LABTECH), by the increased absorbance at 450 nm from the absorbance at 590 nm. Since the increase in absorbance was directly proportional to the amount of total PYY in the unknown sample, the concentration of total PYY could be derived from a standard curve generated from the standards of known PYY concentration.

Statistical Analyses

All data was tested for normality using the D'Agostino & Pearson omnibus normality test and accordingly, central tendencies were calculated and expressed using arithmetic mean±standard error of the mean (SEM). Change in subject weight over the study period was analysed using one-way repeated measures ANOVA. Three hours AUC was calculated for VAS and PYY data. VAS, PYY and food intake data were compared by release location within each macronutrient group using unpaired Student's t-tests. All analyses were two-tailed and conducted using Graphpad Prism (Windows version 6.0) software (San Diego, CA, USA). Statistical significance was set at $p < 0.05$.

Results

Eight participants were included in one study and 76 participants were included in the second study. Nine participants were excluded from overall analysis, due to the inability to measure their ad libitum intake of the test meal and inability to attend the assigned lab visit times.

Sensory Analysis

Figure 2:
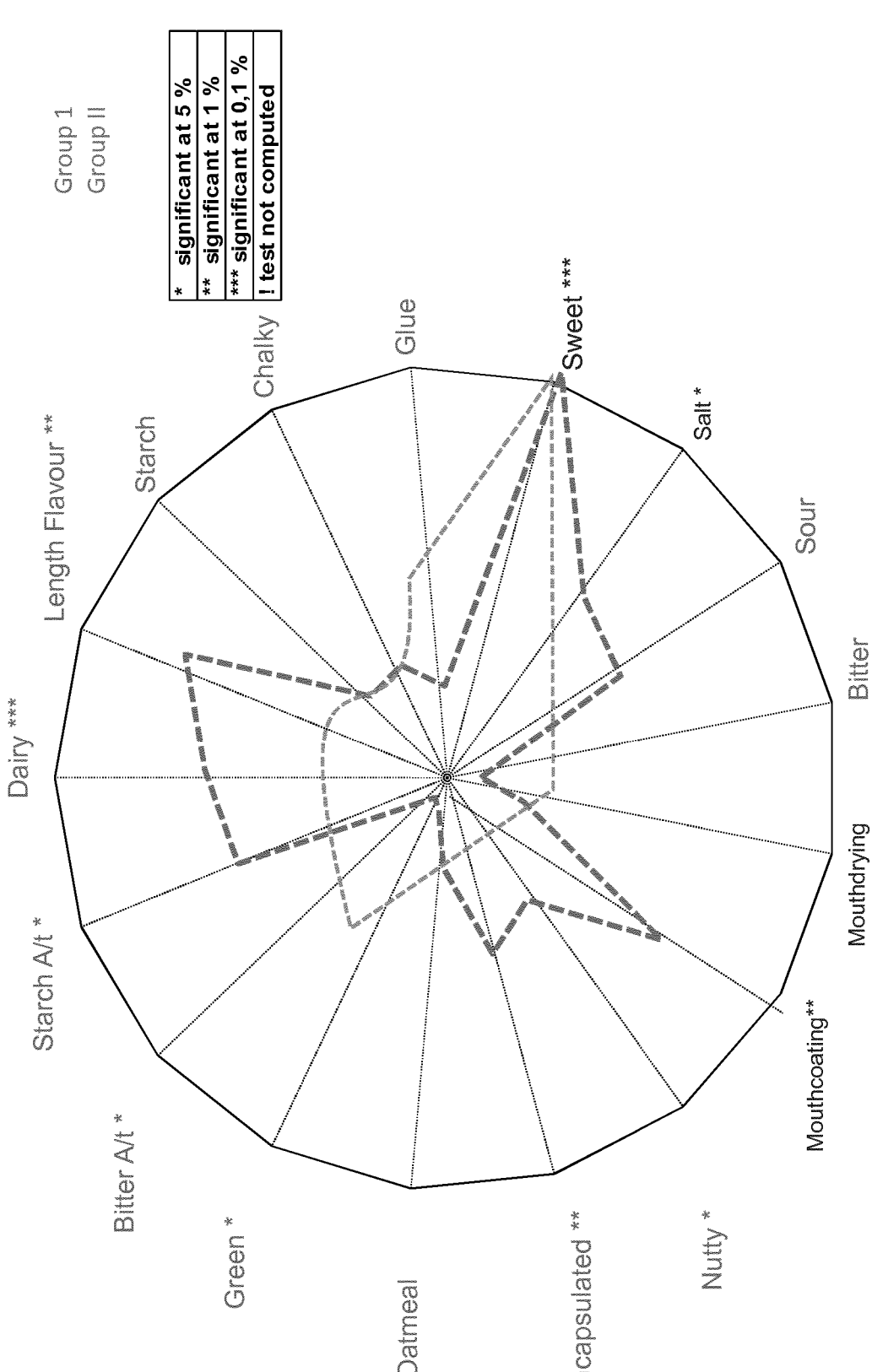
FIG. 2. Sensory Analysis performed further endorsed various organoleptic attributes of the microparticulate material i.e. sweetness

The effects of ingestion of the carbohydrate microparticulates drinks on sensory perception is shown in FIG. 2, relative to free carbohydrate in the same liquid drink The primary outcome was to demonstrate that carbohydrate microparticulates could provide a similar sensory "reward" as that achieved with free carbohydrate loads i.e. free sucrose. The data generated showed an overall liking for the microparticulated carbohydrate with no significant difference relative to free carbohydrate material. For flavour, the taste profile was registered as "sweet" and the aftertaste was registered as "sweet". The data demonstrated an overall acceptance of microparticulated carbohydrate and no significant difference was recognised between free carbohydrate and microparticulated carbohydrate. This data demonstrates that ability to micro-particulate sucrose while maintaining a "sweet" reward without the peak in blood glucose (FIG. 3).

Glucose

Figure 3A:
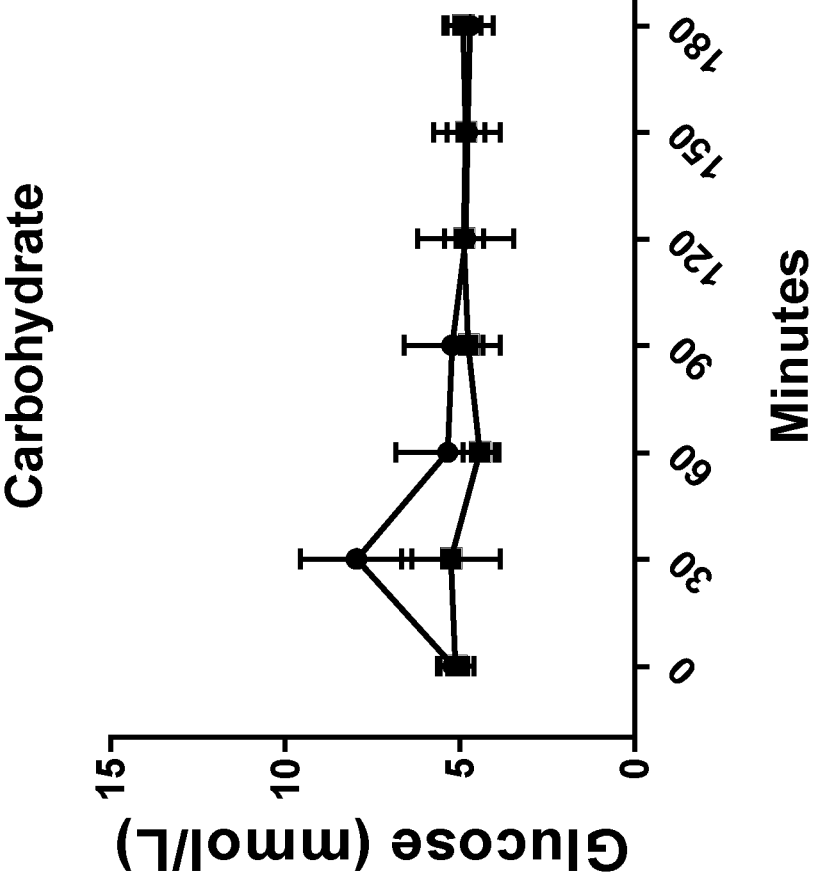
Figure 3B:
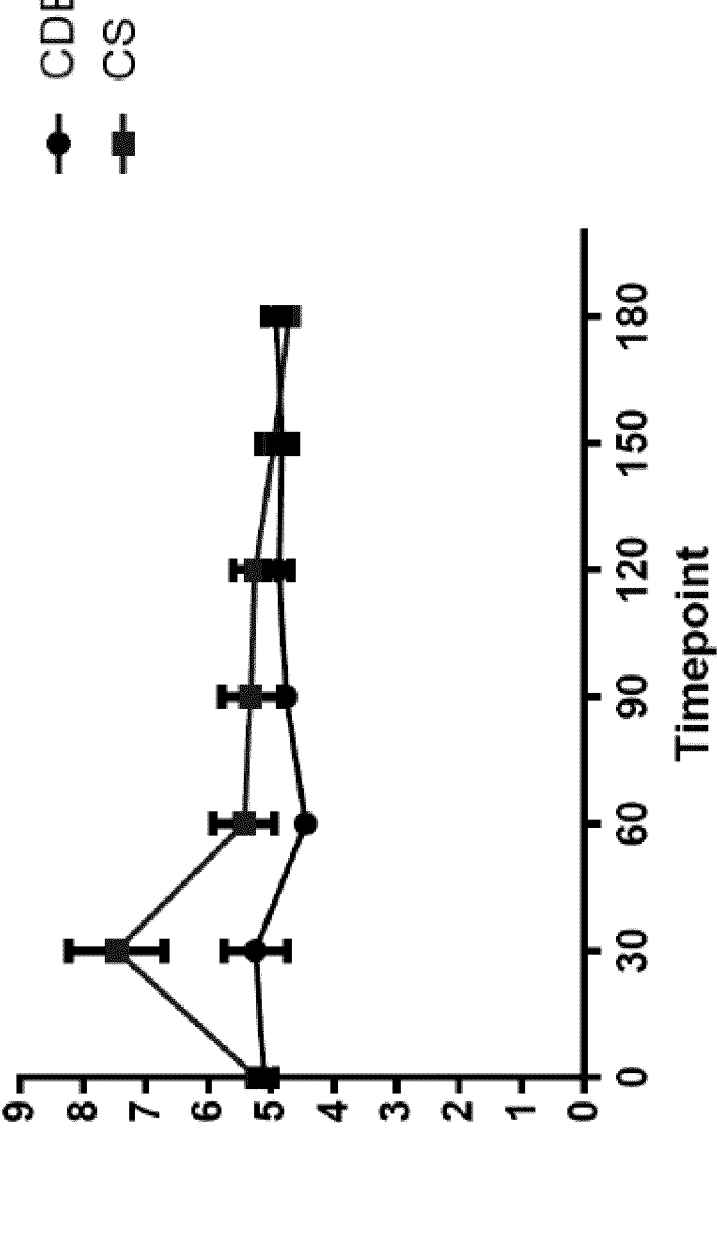
FIG. 3B: Plasma glucose concentration during the period after ingestion of the microparticulated drink (180 min). A significant difference was observed in plasma glucose concentration after ingestion of the microparticulated carbohydrate targeted for release in the stomach relative to microparticulated carbohydrate targeted for release in distal bowel, (n=8) P<0.001. Control group insulin production (FIG. 4) is unable to maintain euglycemic range and so vascular glucose overload is observed. Microencapsulated material leads to a sustained euglycemic concentration due to the lesser absorptive capacity in the distal bowel.
Figure 4A:
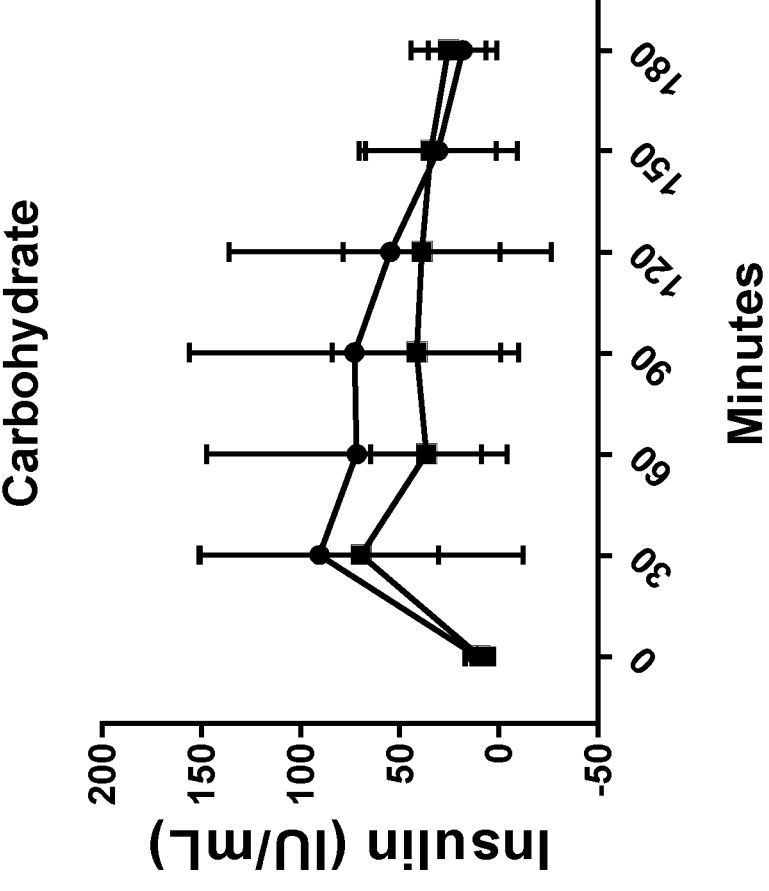
FIG. 4A. Total plasma insulin response measured during the period after ingestion of the microparticulated in a drink (scheduled from 0 to 180 min) containing either carbohydrate microparticulates released in the stomach, or to a test drink containing carbohydrate microparticulates released in the distal bowel. Insulin was measured as IU/mL.
Figure 4B:
FIG. 4B. Insulin concentration in the blood following ingestion of microencapsulated carbohydrate mixture in comparison to control ingredient. Total plasma insulin response measured during the period after ingestion of the microparticulated in a drink (scheduled from 0 to 180 min) containing either carbohydrate microparticulates released in the stomach, or to a test drink containing carbohydrate microparticulates released in the distal bowel. Insulin was measured as IU/mL.
Figure 4B:
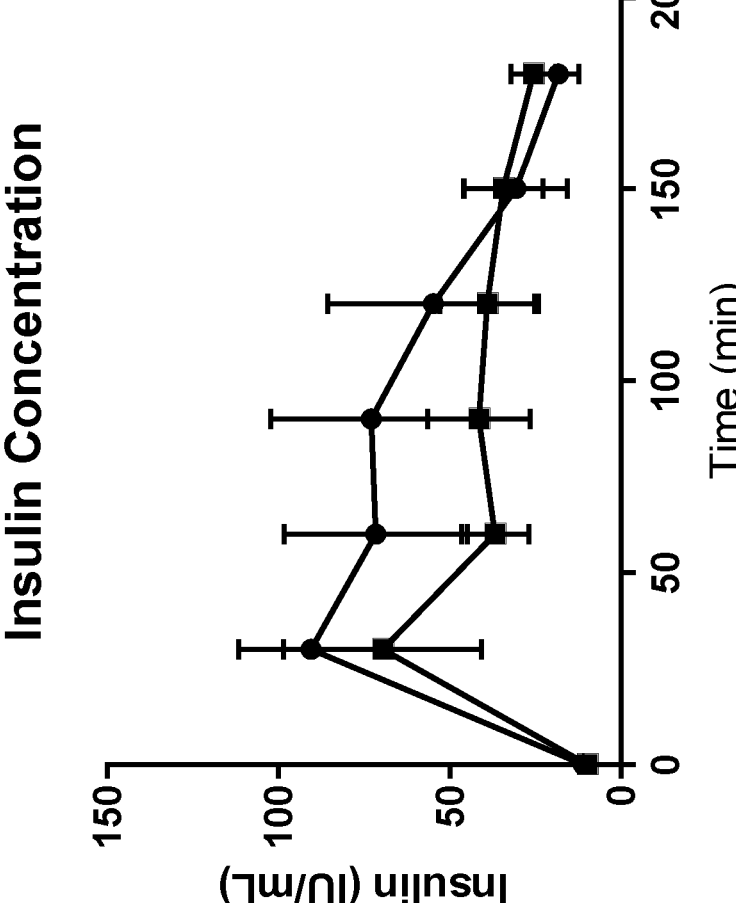

The effects of ingestion of microparticulated carbohydrate drink or control drinks on plasma glucose concentrations are presented in FIG. 3. A dramatic increase in AUC of the plasma glucose concentration was observed after consumption of the control drink (targeted release to the stomach) relative to with microparticulated carbohydrate targeted for the distal ileum. A significant difference was observed in plasma glucose concentration after ingestion of the microparticulated carbohydrate targeted for release in the stomach relative to microparticulated carbohydrate targeted for release in distal bowel, $P < 0.0001$. Linked with the effect of a "sweet" sensory profile, microparticulated carbohydrate targeted for release in the distal ileum had shown the ability to regulate post-prandial blood sugar levels while mimicking the "sweet" taste of regular simple carbohydrates i.e. sucrose.

Insulin Response

Total plasma insulin measured as IU/mL showed a significant improved sensitivity after ingestion of the microparticulated carbohydrate targeted for release in the distal ileum relative to microparticulated carbohydrate targeted for release in stomach, $P < 0.01$. This data demonstrates the ability to maintain glucose homeostasis using microparticulated carbohydrate targeted for release in distal bowel. This shows that encapsulated carbohydrate targeted for the distal bowel has the ability to increase insulin sensitivity/glucose responses.

PYY Response

In FIG. 5, total plasma PYY is measured as a function of time after ingestion of the microparticulated drink. Data demonstrated no significantly difference in AUC PYY response in the distal bowel compared to the stomach ($p = 0.40$ respectively) at the time of administration and ingestion ($t = 0$). No difference in AUC total plasma PYY response was seen after administration (FIG. 6) and for a total of 150 min (FIG. 5) following administration of carbohydrate microparticulates targeted for stomach or carbohydrate microparticulates targeted for the distal bowel (p=0.63; p=0.40 respectively) (FIG. 6).

However, after 180 min, ELISA PYY results from microparticulated drinks showed a significant increase relative to the control drink (FIG. 7). With sufficient time to allow the transit of microparticulates of carbohydrate through the GI system of the participant, FIGS. 5 and 7 showed a significant difference in mean PYY plasma concentration (pg/ml) between the release locations (p=0.22; p=0.16 respectively) of stomach and distal bowel. Hence, this further endorses the benefits of the ileal delivery where gut peptide hormones elicit there effects for glucose and satiety effects.

These carbohydrate microparticulates can have a range of sizes are shown in FIGS. 8A and 8B and the novel drying technology used helps to generate a non-porous outer shell of a dry carbohydrate microparticulate, which protects against gastric and other conditions (FIG. 8C). This data further endorses the commercial applicability of this technology to support a various product categories i.e. microparticulates/micro-capsules can be produced in a range of sizes to meet specific product application criteria for blending/fortification.

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of regulating post-prandial blood sugar levels in a diabetic or pre-diabetic subject, the method comprising orally administering to the subject a composition comprising or consisting of microparticles comprising a high glycaemic index (GI) carbohydrate contained within a gastric-resistant, ileal-sensitive, non-porous carrier configured for release of the high GI carbohydrate in the distal ileum, in which the non-porous carrier comprises polymerised protein in an amount sufficient to inhibit degradation of the microparticles in the duodenum at least 48 minutes after oral administration, and in which the microparticles release the high GI carbohydrate in the distal ileum wherein the microparticles have two coats of polymerised denatured protein.

2. A method of normalising blood glucose homeostasis in a diabetic or pre-diabetic subject, the method comprising orally administering to the subject a composition comprising or consisting of microparticles comprising a high glycaemic index (GI) carbohydrate contained within a gastric-resistant, ileal-sensitive, non-porous carrier configured for release of the high GI carbohydrate in the distal ileum, in which the non-porous carrier comprises polymerised protein in an amount sufficient to inhibit degradation of the microparticles in the duodenum at least 48 minutes after oral administration, and in which the microparticles release the high GI carbohydrate in the distal ileum wherein the microparticles have two coats of polymerised denatured protein.

3. A method of increasing or stimulating a GLP-1 response in a subject having a metabolic disorder characterised by dysregulated insulin production, the method comprising orally administering to the subject a composition comprising or consisting of microparticles comprising high glycaemic index (GI) carbohydrate contained within a gastric-resistant, ileal-sensitive, non-porous carrier configured for release of the high GI carbohydrate in the distal ileum, in which the non-porous carrier comprises polymerised protein in an amount sufficient to inhibit degradation of the microparticles in the duodenum at least 48 minutes after oral administration, and in which the microparticles release the high GI carbohydrate in the distal ileum wherein the microparticles have two coats of polymerised denatured protein.

4. A method according to claim 2, in which the subject has Type II diabetes.

5. A method according to claim 1, in which the polymerised protein is denatured or hydrolysed protein.

6. A method according to claim 1, in which the polymerised protein is dairy or plant protein.

7. A method according to claim 1, in which the composition is administered 1 to 3 hours before a meal.

8. A method according to claim 1, in which the microparticle has a core-shell morphology with a high GI carbohydrate core in which the carrier comprises a membrane surrounding the core.

9. A method according to claim 1, in which the core consists essentially of high GI carbohydrate.

10. A method according claim 1, in which the non-porous carrier comprises a matrix and in which the high GI carbohydrate is dispersed throughout the matrix.

11. A method according to claim 1, in which the high GI carbohydrate is in solid or liquid form.

12. A method according to claim 1, in which the composition is in a unit dose form, in which the unit dose composition comprises 100 to 1000 Kcal of high GI carbohydrate contained within the microparticles.

13. A method according to claim 1, in which the high GI carbohydrate is a disaccharide.

14. A method of providing sustained energy release over time in a healthy subject, the method comprising orally administering the composition to the subject, the composition comprising or consisting of microparticles comprising a high glycaemic index (GI) carbohydrate contained within a gastric-resistant, ileal-sensitive, non-porous carrier configured for release of the high GI carbohydrate in the distal ileum, in which the non-porous carrier comprises polymerised protein in an amount sufficient to inhibit degradation of the microparticles in the duodenum at least 48 minutes after oral administration, and in which the microparticles release the high GI carbohydrate in the distal ileum wherein the microparticles have two coats of polymerised denatured protein.

15. A method according to claim 14, in which the non-porous carrier comprises polymerised hydrolysed denatured protein.

16. A method according to claim 14, in which the non-porous carrier comprises polymerised plant protein.

17. A method according to claim 14, in which the composition is administered 1 to 3 hours before a meal.

18. A method according to claim 14, in which the composition is provided in a unit dose form, and in which the composition comprises 100 to 1000 Kcal of the high GI carbohydrate that is contained within the microparticles.

19. The method of claim 1, wherein the regulating of the post-prandial blood sugar levels in the subject comprises attenuating or inhibiting spikes in the post-prandial blood sugar levels in the subject compared to spikes in post-prandial blood sugar levels of a subject orally administered a composition containing the same type and amount of carbohydrate in which the carbohydrate is not protected from gastric release.

20. A method of regulating post-prandial blood sugar levels in a diabetic or pre-diabetic subject, the method comprising orally administering to the subject a composition comprising or consisting of microparticles comprising a high glycaemic index (GI) carbohydrate contained within a gastric-resistant, ileal-sensitive, non-porous carrier configured for release of the high GI carbohydrate in the distal ileum, in which the non-porous carrier comprises polymerised protein in an amount sufficient to inhibit degradation of the microparticles in the duodenum at least 48 minutes after oral administration, and in which the microparticles release the high GI carbohydrate in the distal ileum wherein the microparticles have two coats of polymerised denatured protein and wherein the microparticles are formed by a method comprising the steps of:

providing solid carbohydrate microparticles on a fluidised bed;

spraying a denatured protein solution onto the bed to coat the carbohydrate particles and form microparticles; and drying the microparticles, wherein a second denatured protein solution is sprayed on to the dried microparticles.

* * * * *